United States Patent
Ono et al.

(10) Patent No.: US 6,756,482 B1
(45) Date of Patent: Jun. 29, 2004

(54) PURIFIED HUMAN ACTIVIN AND PROCESS FOR PRODUCING THE SAME

(75) Inventors: Kunio Ono, Kawasaki (JP); Shigekatsu Tsuchiya, Kawasaki (JP); Daisuke Ejima, Kawasaki (JP); Yuzuru Eto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 256 days.

(21) Appl. No.: 09/721,750

(22) Filed: Nov. 27, 2000

Related U.S. Application Data

(63) Continuation of application No. PCT/JP99/02680, filed on May 20, 1999.

(30) Foreign Application Priority Data

May 25, 1998 (JP) .......................................... 10-159943

(51) Int. Cl.[7] .................. A61K 38/24; C07K 14/00; A23J 1/00
(52) U.S. Cl. ............ 530/399; 530/412; 530/413; 530/416; 530/419; 530/422; 530/424; 530/427
(58) Field of Search ............................ 530/399, 412, 530/413, 416, 419, 422, 424, 427

(56) References Cited

U.S. PATENT DOCUMENTS

| | | | | |
|---|---|---|---|---|
| 4,774,322 A | * | 9/1988 | Seyedin et al. | 530/353 |
| 5,047,510 A | * | 9/1991 | Cone et al. | 530/399 |
| 6,084,076 A | | 7/2000 | Ejima et al. | 530/399 |

FOREIGN PATENT DOCUMENTS

| | | | |
|---|---|---|---|
| EP | 0 323 842 | | 7/1989 |
| EP | 0 323 842 | * | 12/1989 |
| JP | 145197 | | 5/1994 |
| WO | WO 92/14481 | * | 9/1992 |
| WO | WO 92/19252 | | 11/1992 |
| WO | WO 97/23628 | | 7/1997 |

OTHER PUBLICATIONS

Takeichi Horio in Fundamental Experimental Method of Protein Enzyme, p. 63, rev. 2, published by Nankodo, 1994.*
Eto et al., (Biochemical and Biophysical Research Communications, vol. 142, No. 3, pp. 1095–1103, Feb. 13, 1987.*
Murata et al., (Biochemical and Biophysical Research Communications, vol. 151, No. 1, pp. 230–235, Feb. 29, 1988.*
R. Fei, et al., Shengwu Huaxue Zazhi, vol. 8, No. 1, pp. 121–128, "Purification and Characterization of Mammalian (Rabbit) Erythroid Differentiation Factor (EDF)", 1992 (Chemical Abstract only).
A. Fukui, et al., Dev. Biol., vol. 159, No. 2, pp. 131–139, "Isolation and Characterization of Xenopus Follistatin and Activins", 1993 (Chemical Abstract only).

* cited by examiner

*Primary Examiner*—Christopher S. F. Low
*Assistant Examiner*—Abdel A. Mohamed
(74) *Attorney, Agent, or Firm*—Oblon, Spivak, McClelland, Maier & Neustadt, P.C.

(57) ABSTRACT

The present invention provides a process for purifying human activin by cation exchange chromatography and chaotropic ion concentration gradient elution.

16 Claims, 8 Drawing Sheets

Molecular Weight 94000 
67000
43000

30000

20000

14400

Lane No.   1   2   3

PURIFIED HUMAN ACTIVIN AND PROCESS FOR PRODUCING THE SAME

This application is a Continuation of International Application number PCT/JP99/02680, filed on May 20, 1999.

BACKGROUND OF THE INVENTION

1. Field of the Invention

The present invention relates to an novel purified human activin. More specifically, the present invention relates to a human activin with an improved purity and a process for producing the same, particularly a process to isolate and purify human activin A from crude human activin A. Furthermore a highly purified human activin which can be obtained by such a process, and the human activin which is in a form of drug product.

2. Description of the Related Art

It is desirable to develop human activin as a medicine. Particularly, human activin A is a useful substance for the amelioration or treatment of osteoporosis or other use.

Human activin A is a homo-dimer protein consisting of two polypeptide chains of 116 amino acid residues respectively, which is isolated and purified from the culture supernatant of human leukemia cell line THP-1 (IFO 50147). The molecular weight of human activin A is about 25,000 daltons, 9 cysteine residues (Cys) exist in every polypeptide chain (total 18 residues in dimer), and total 9 disulfide bonds are formed intra- and intermolecularly (refer to Biochemical and Biophysical Research Communications, 142, 1095–1103, 1987).

The present inventors, in particular, have been developing the following four methods for the production and purification of human activin A. That is:

(1) a method for obtaining human activin A by ammonium sulfate fractionation and 4 steps of column chromatography from the culture supernatant of human leukemia cell line THP-1 (IFO 50147) after stimulating with phorbol ester (refer to Cell Technology, a separate volume 4, p.48–58, 1987);

(2) a method for obtaining human activin A by the combination of acid-organic solvent precipitation/cooling phase separation, and reverse-phase HPLC, from the culture supernatant of recombinant a CHO cell which is overproducing human activin A, obtained by introducing the expression vector in which the human activin cDNA was integrated (refer to Biochemical and Biophysical Research Communications, 151, 230–235, 1988; and Japanese Patent Kokai Publication JP-A-01-300898);

(3) a method for obtaining human activin A by affinity chromatography using follistatin, a human activin A binding protein as a ligand, from the culture supernatant obtained by the same method as described above (refer to Japanese Patent Kokai Publication JP-A-02-255098), and (4) a method for obtaining human activin A by reverse-phase HPLC from crude human activin A solution which is obtained by solubilizing and refolding an inclusion body accumulated in the cell of recombinant microorganisms overproducing human activin A, to which the expression vector integrated human activin A CDNA was introduced (refer to WO97/23638).

The human activin A obtained by the four methods described above was pure enough for animal experimentation. However, for developing human activin A as a drug product, the practical purification process which can produce extremely high purity bulk of the drug product for pharmaceutical use in humans with industrial scale and appropriate production cost, has to be constructed. It was difficult to purify human activin A with enough purity for injecting to humans in the methods described above. Namely, it was impossible to remove completely an antigenic substance and a pyrogen etc. derived from a host or a medium, molecular variants based on the translational mistake or inappropriate post-translational processing of human activin A gene, and degradation, modification and the like products of human activin A produced in the purification process, even if the chromatography used in the four production methods described above may be combined in any way.

In view of these situations, a process for producing a highly purified human activin is desirable.

It is a problem to be solved by the present invention to develop a process in which a highly pure human activin A appropriate for pharmaceutical use from crude human activin, particularly crude human activin A, can be isolated and purified easily. Moreover, the activin can be produced on an industrial scale as highly pure human activin.

SUMMARY OF THE INVENTION

The present inventors have studied eagerly to solve the problem described above and have investigated crude human activin A as a crude human activin thoroughly.

It is considered to be most preferable to establish an ion exchange chromatography by using the difference in electrostatic character between human activin A and its variants to separate the human activin A from the crude human activin A solution obtained by refolding the inclusion body in the culture of recombinant microorganisms overproducing human activin A. For this reason, it is thought that the ion exchange chromatography is easy for up-scaling compared to reverse-phase chromatography and it is most suitable method for industrial large scale production of protein.

Eto et al. purified crude human activin A by anion exchange chromatography using two carriers such as DEAE-toyopearl (TOSOH Corp.) and Mono-Q (Amersham Pharmacia Biotech Limited) (refer to Biochemical and Biophysical Research Communications, 151, 230–235, 1988). However, when DEAE-toyopearl which is a packing material of column for large scale purification was used for purification, protein purity of human activin A thus obtained is low, ca. 2%. Even if Mono-Q, which is a column for high performance liquid chromatography (HPLC) with higher efficiency, was used, the protein purity was up to ca. 55%. Either method was not sufficient to get the purified protein appropriate for pharmaceutical use. In addition, when either column was used, the recovery of human activin A was low (ca. 56% for the former recovery, and ca. 63% for the latter recovery), and it was decided that these columns could not be used for industrial production as they were, because the recovered solution was very dilute. It was quite clear that the purification of human activin A by an ion exchange chromatography using conventional purification techniques in the industrial scale as described above, was extremely difficult.

In order to solve the above mentioned problem, the present inventors have proceeded the research and have found a method to purify human activin A to that of high purity from a crude human activin A solution by using the purification process involving a cation exchange chromatography, after removing low molecular weight impurities therefrom, if necessary, and finally completed the present invention based on these findings.

More precisely, according to the present invention, a highly pure human activin A can be obtained by the process which comprises removing the refolding agents in the crude human activin, especially the crude human activin A solution by the standard method, if they remain and it necessary, applying it (preferably containing a high concentration of organic solvent) to a cation exchange column equilibrated with the buffer solution of chaotropic ion and very low pH, and separating and removing a variant different in electrostatic character from the activin by concentration gradient elution method of chaotropic ion, with high efficiency.

Namely, when a microorganism to which the human activin A gene is introduced, is cultivated, and an active and a crude human activin A solution obtained by solubilizing and refolding the inclusion body of the human activin A thus produced is used for purification, by applying such solution to a cation exchange chromatography preferably in the condition combined with a high concentration of organic solvent, extremely low pH value, and a salt of chaotropic ion character, preferably after removing low molecular weight impurities therefrom, performing a chaotropic ion concentration gradient elution therefor, it is possible to remove effectively, more preferably, any impurities of a protein derived from a host, a non-refolded aggregate and a variant different in electrostatic character from the activin, and moreover obtain a concentrated human activin A with high recovering yield.

That is, the present invention is directed to a process for producing human activin with an improved purity, which comprises subjecting a crude human activin to a purification procedure involving a cation exchange chromatography, in particular, a cation exchange chromatography by a concentration gradient elution method. For the concentration gradient elution method, a chaotropic ion concentration gradient elution method is preferable.

As a representative example of human activin, human activin A can be exemplified.

Furthermore, the present invention contains the following embodiments:

[1] The process according to the process for the production described above, wherein the cation exchange chromatography is performed in the presence of water soluble organic solvent and/or in the acid condition.

[2] The process according to the process for the production described above [1], wherein in the purification method, the organic solvent contains at least one member selected from the group consisting of lower alcohol, acetonitrile, dimethyl sulfoxide and dimethylformamide, and its concentration is at least 20 volume %, more preferably 20 to 60 volume %.

[3] The process according to the process for the production described above, wherein the crude human activin contains at least one member selected from the group consisting of a variant different in electrostatic character from the activin, a protein derived from a host, an antigenic substance and a pyrogen etc. derived from a host and/or a medium, non-refolded aggregates in case of refolding, molecular variants based on the translational mistake and/or inappropriate post-translational processing of the gene (human activin A), and degradation, modification and the like products of human activin produced in the purification process.

[4] The process according to the process for the production described above, wherein the crude human activin contains at least one species in the impurities derived from an active and a crude human activin obtained by solubilizing and refolding an inclusion body of human activin produced by cultivating a microorganism to which the human activin A gene is introduced.

[5] The process according to the process for the production described above, wherein purification process for removing low molecular weight impurities is combined thereto as a purification process.

[6] The process for the production described above, involving further purification process by anion exchange chromatography under the alkaline condition.

[7] The process according to the process for the production described above [6], wherein the chromatography contains an anion exchange chromatography having natural polysaccharide as a base matrix.

[8] A process for producing a concentrated human activin at a high recovering yield, which comprises cultivating a microorganism to which the human activin gene is introduced, solubilizing and refolding the inclusion body of the human activin in thus produced, removing low molecular weight impurities from the active and crude human activin solution obtained above, applying this to a cation exchange chromatography equilibrated with the solution of extremely low pH value containing high concentration of organic solvent and chaotropic ion, and performing the chaotropic ion concentration gradient elution to remove a protein derived from a host, a non-refolded aggregate and a variant different in electrostatic character from the activin are removed effectively and highly.

[9] In the process for the production described above [8], the process for producing human activin with high purity, from the crude human activin solution, which comprises removing low molecular weight impurities from the solution, and combining the following 2 steps to purify it more effectively:

(i) A step for recovering concentrated human activin A quantitatively, which comprises applying said partially purified product to an anion exchange chromatography having natural polysaccharide as a base matrix, equilibrated under the extremely high pH condition, and substituting the buffer solution of higher salt concentration and lower pH value, added with organic solvents therefor, to remove almost all of a protein derived from a host, a non-refolded aggregate and a variant different in electrostatic character from the activin;

(ii) A step for obtaining concentrated human activin A with high recovering yield, which comprises substituting for the buffer solution of the fraction recovered in the above process (i), applying it to an anion exchange chromatography equilibrated with extremely high pH solution containing organic solvent, and performing an elution with the salt concentration gradient and pH gradient (lowering pH) to remove almost all of a protein derived from a host and a variant different in electrostatic character from the activin, followed by the step for the purification process of the above described cation exchange chromatography, after substituting for the buffer solution of the recovered fraction obtained in the above (ii).

[10] A human activin with improved purity and a highly purified human activin having a purity of at least 99%, obtained by the process for the production of the present invention and that of [1] to [9] described above.

[11] A human activin having a purity of at least 99%, which contains substantially no variant different in electrostatic characters from the activin, as impurity.

[12] In the processes for the production of the present invention and that of [1] to [9] described above, as well as those of [10] and [11] described above, the inventions wherein the human activin is a human activin A.

[13] An agent for amelioration or treatment of osteoporosis or other drug products comprising the human activin with improved purity, in particular, such human activin A, which is the present invention or which is obtained or can be obtained by the present invention.

BRIEF DESCRIPTION OF THE DRAWINGS

A more complete appreciation of the invention and many of the attendant advantages thereof will be readily obtained as the same becomes better understood by reference to the following Figures in conjunction with the detailed description below.

6 mg of human activin A dissolved in 1.8 mM HCl were applied to a cation exchange chromatography (Resource-S; Amersham Pharmacia Biotech Limited), and subjected to the salt concentration gradient elution. The fraction indicated by "–" in the figure, was recovered.

Figure 1A:
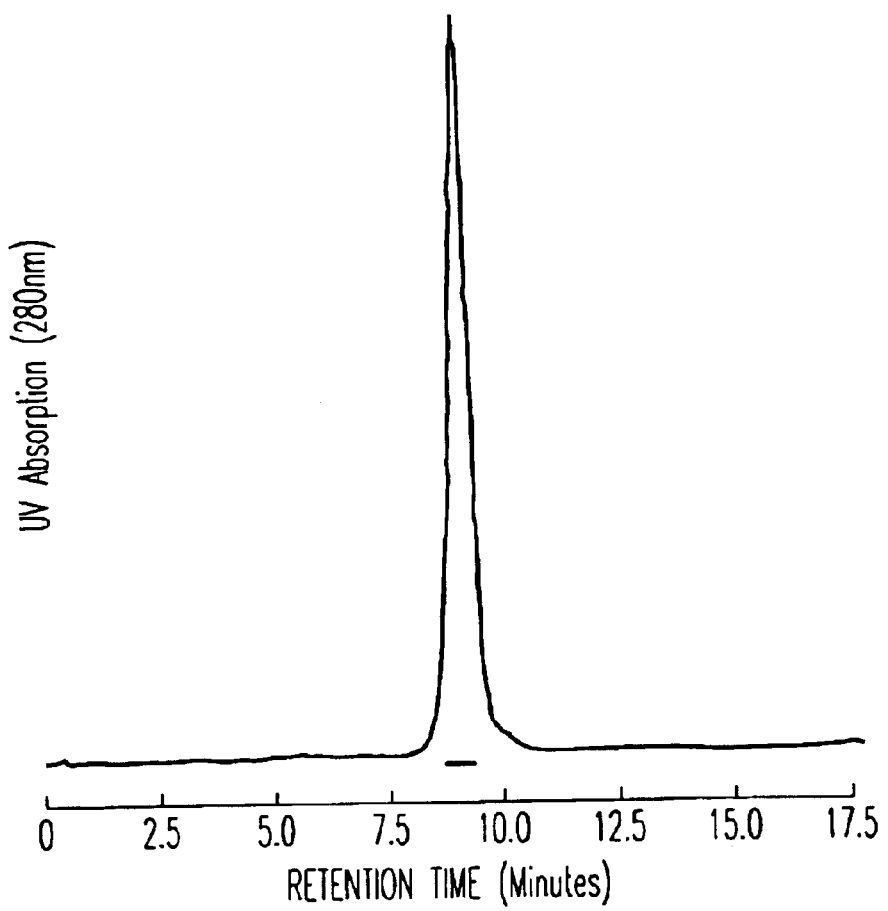
FIG. 1 shows the result of a cation exchange chromatography performed in Example 1 of the present invention. The horizontal axis shows the retention time (minutes).
Figure 1B:
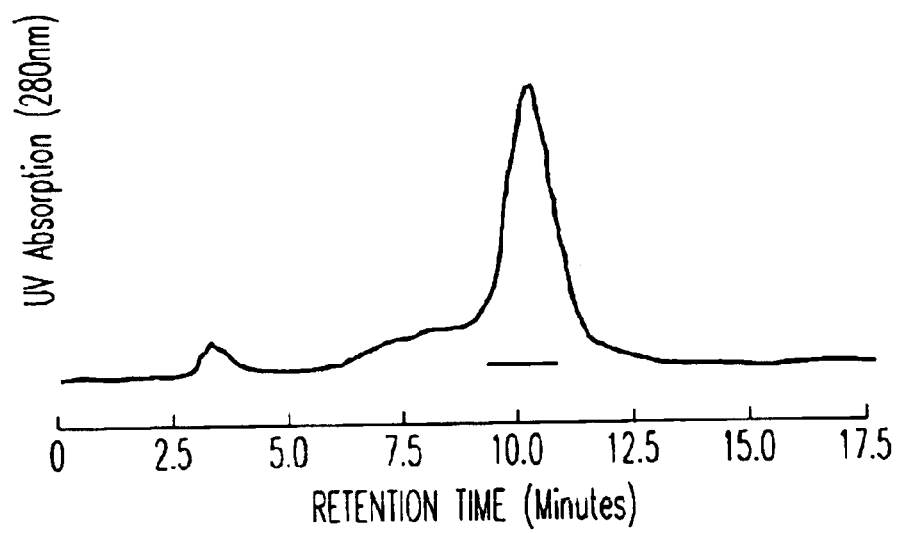

In FIG. 1, (a) showed the result of NaCl concentration gradient elution method and (b) showed that of $NaClO_4$ concentration gradient elution method.

Figure 2:
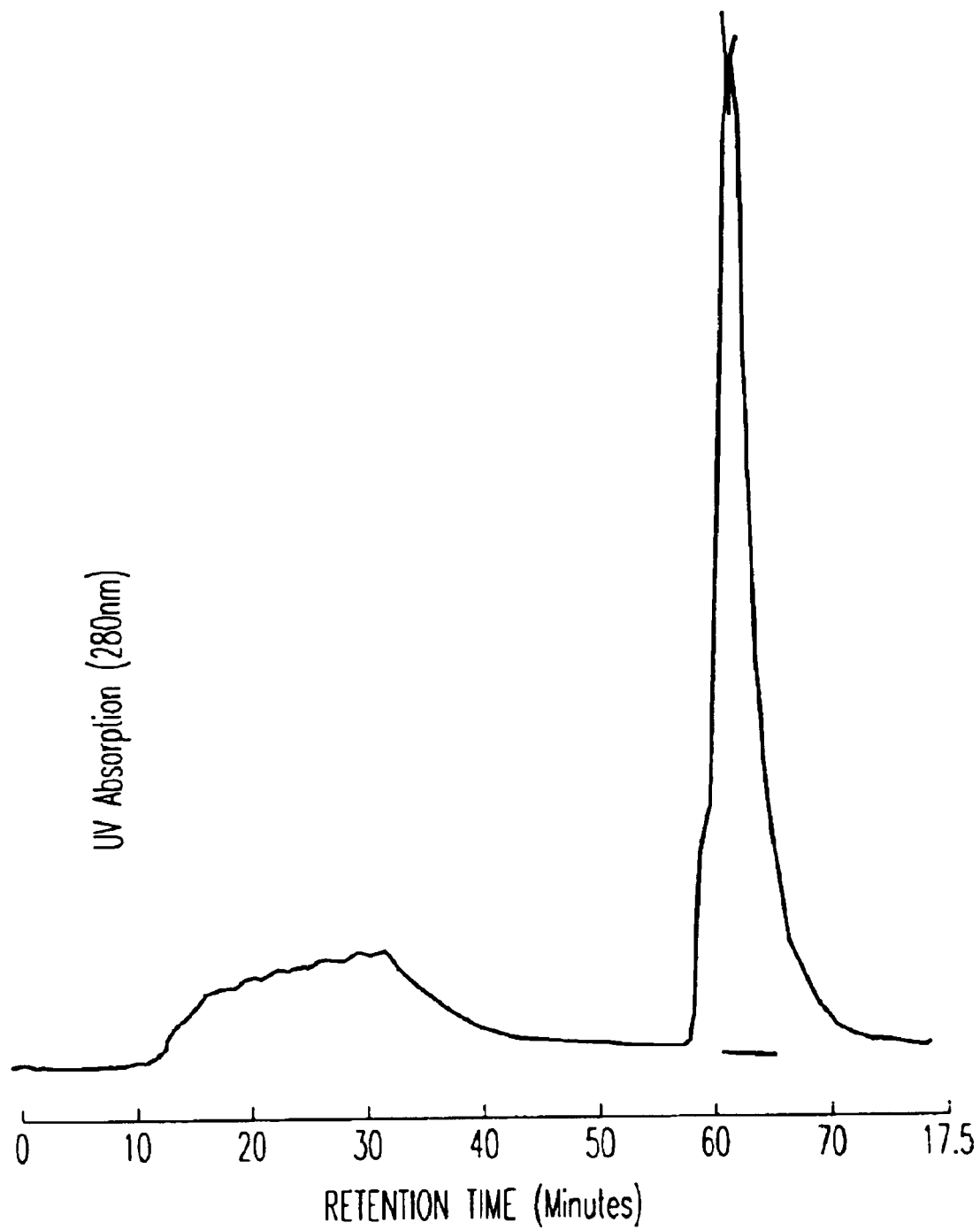

FIG. 2 shows the result of an anion exchange chromatography performed in Example 2. The horizontal axis shows the retention time (minutes).

36 mg of human activin A dissolved in 20 mM 1,3-diaminopropane/HCl containing 20 mM NaCl were applied to an anion exchange chromatography (Q-Sephalose FF; Amersham Pharmacia Biotech Limited), and the buffer solution was changed to 12% acetonitrile, 0.1 M NaCl, and 20 mM 1,3-diaminopropane/HCl. The fraction indicated by "–" in the figure, was recovered.

Figure 3:
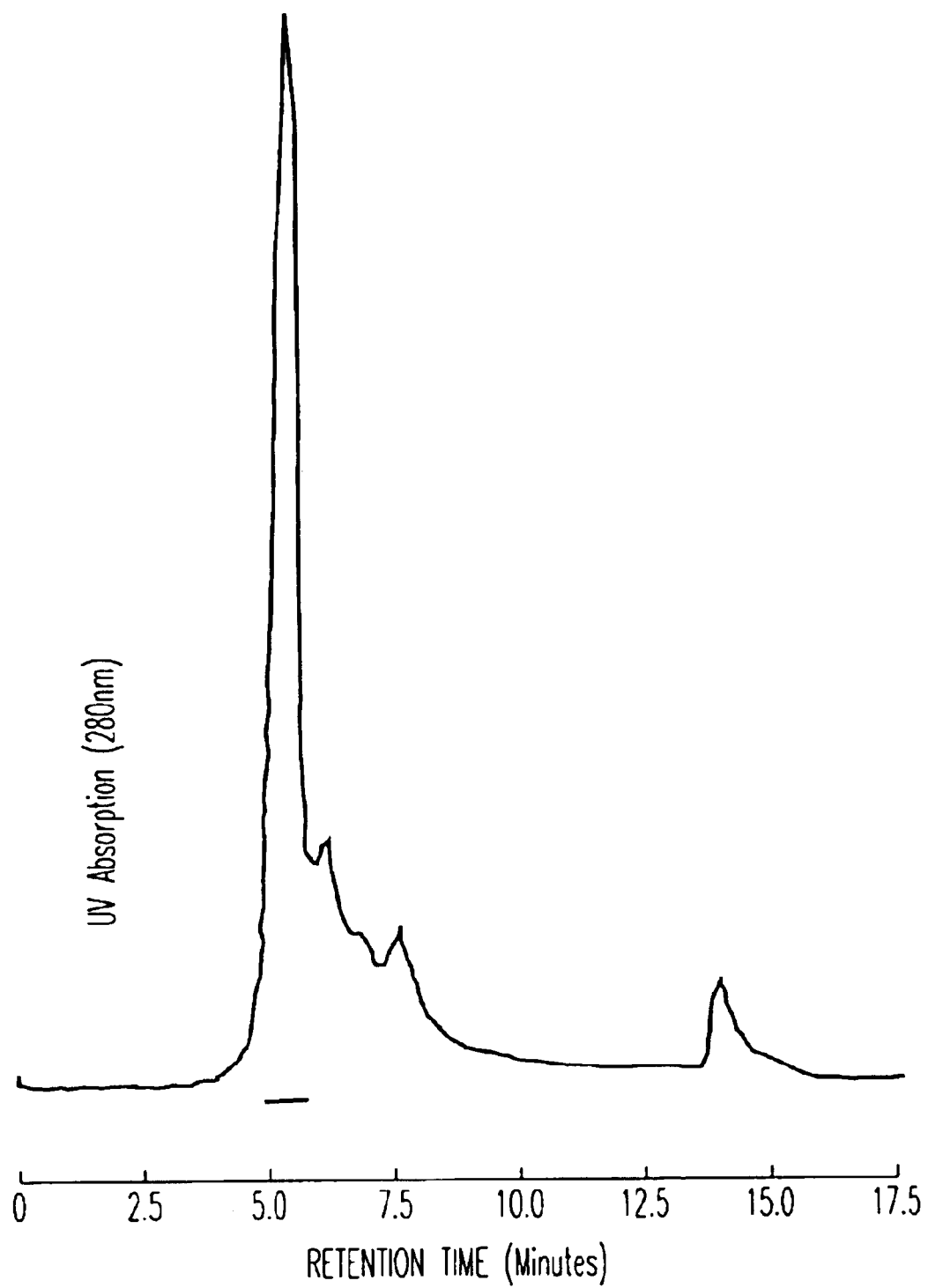

FIG. 3 shows the result of second time of anion exchange chromatography performed in Example 2. The horizontal axis shows the retention time (minutes).

6 mg of human activin A dissolved in 20 mM 1,3-diaminopropane/HCl were applied to an anion exchange chromatography (Resource-Q; Amersham Pharmacia Biotech Limited), and subjected to the elution with the salt concentration and pH gradients.

Figure 4:
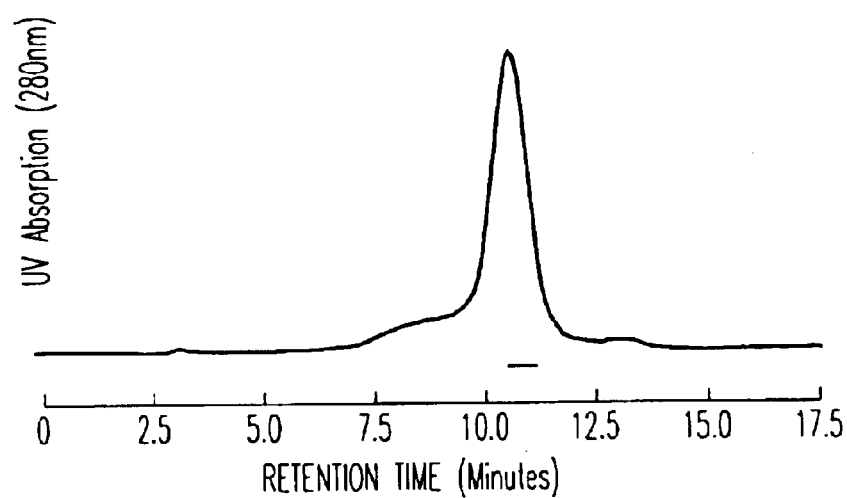

FIG. 4 shows the result of a cation exchange chromatography performed in Example 2. The horizontal axis shows the retention time (minutes).

6 mg of human activin A dissolved in 1.8 mM HCl were applied to a cation exchange chromatography (Resource-S; Amersham Pharmacia Biotech Limited), and subjected to the salt concentration gradient elution. The fraction indicated by "–" in the figure, was recovered.

Figure 5:
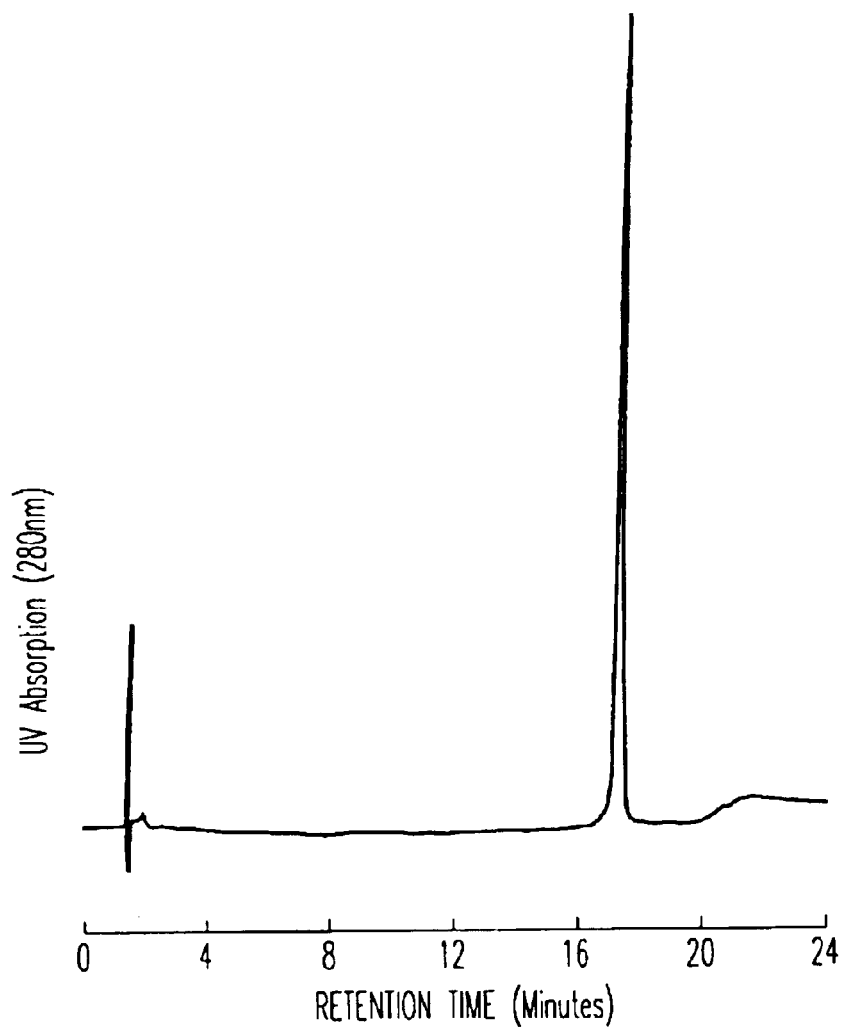

FIG. 5 shows the result of a reverse-phase HPLC of purified human activin A fraction, performed in Example 2. The horizontal axis shows the retention time (minutes).

7 μg of purified human activin A were applied to a reverse-phase HPLC (Nucleosil C8; GL Science Co.) and subjected to the elution with acetonitrile concentration gradient.

The peak detected at ca. 17.5 min. of retention time corresponds to that of human activin A.

Figure 6:
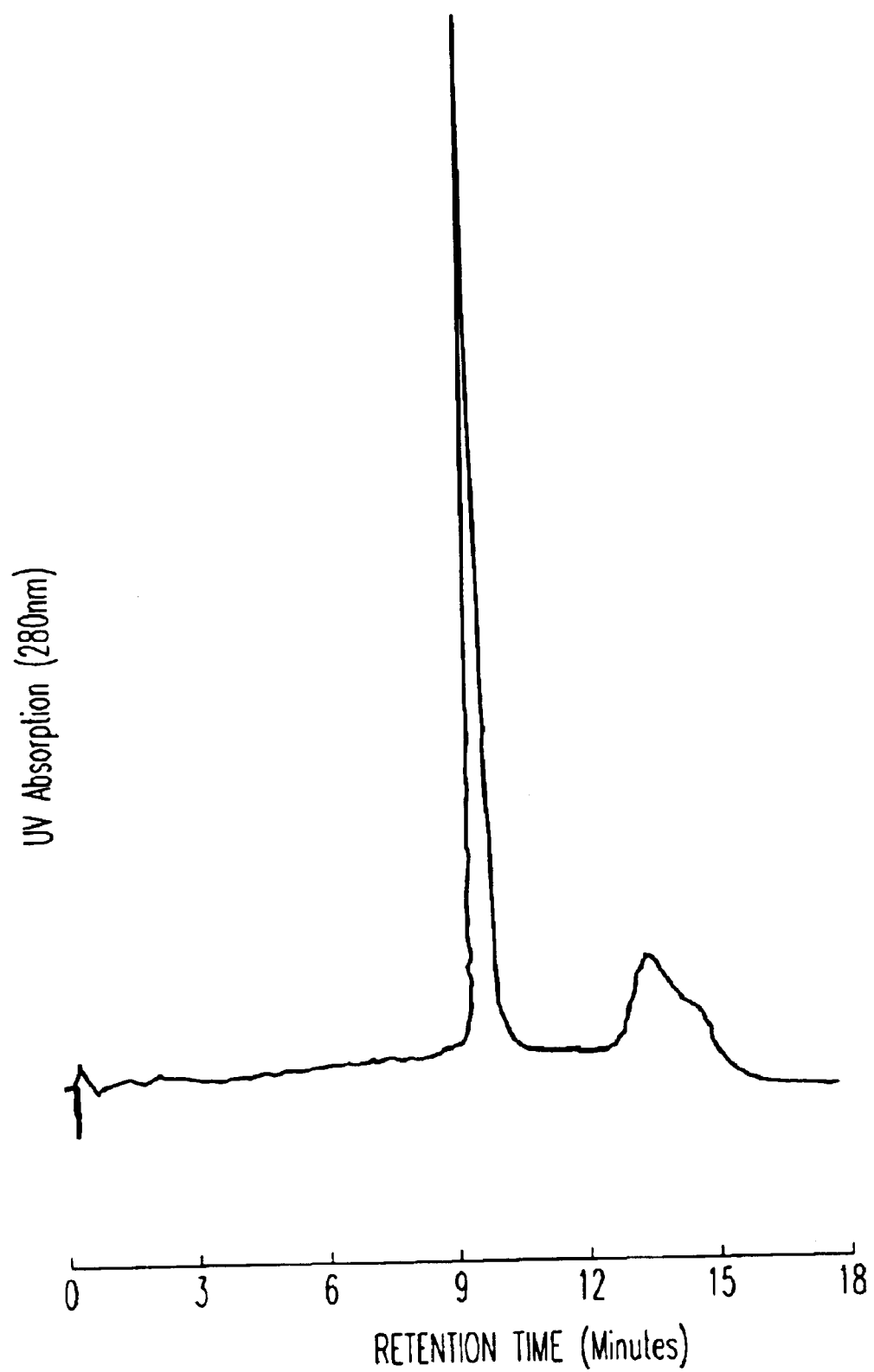

FIG. 6 shows the result of a cation exchange HPLC of purified human activin A fraction, performed in Example 2. The horizontal axis shows the retention time (minutes).

12 μg of purified human activin A were applied to a cation exchange HPLC (SP-NPR; TOSOH Corp.) and subjected to the elution with salt concentration gradient. The peak detected at ca. 10 min. of retention time corresponds to that of human activin A.

Figure 7:
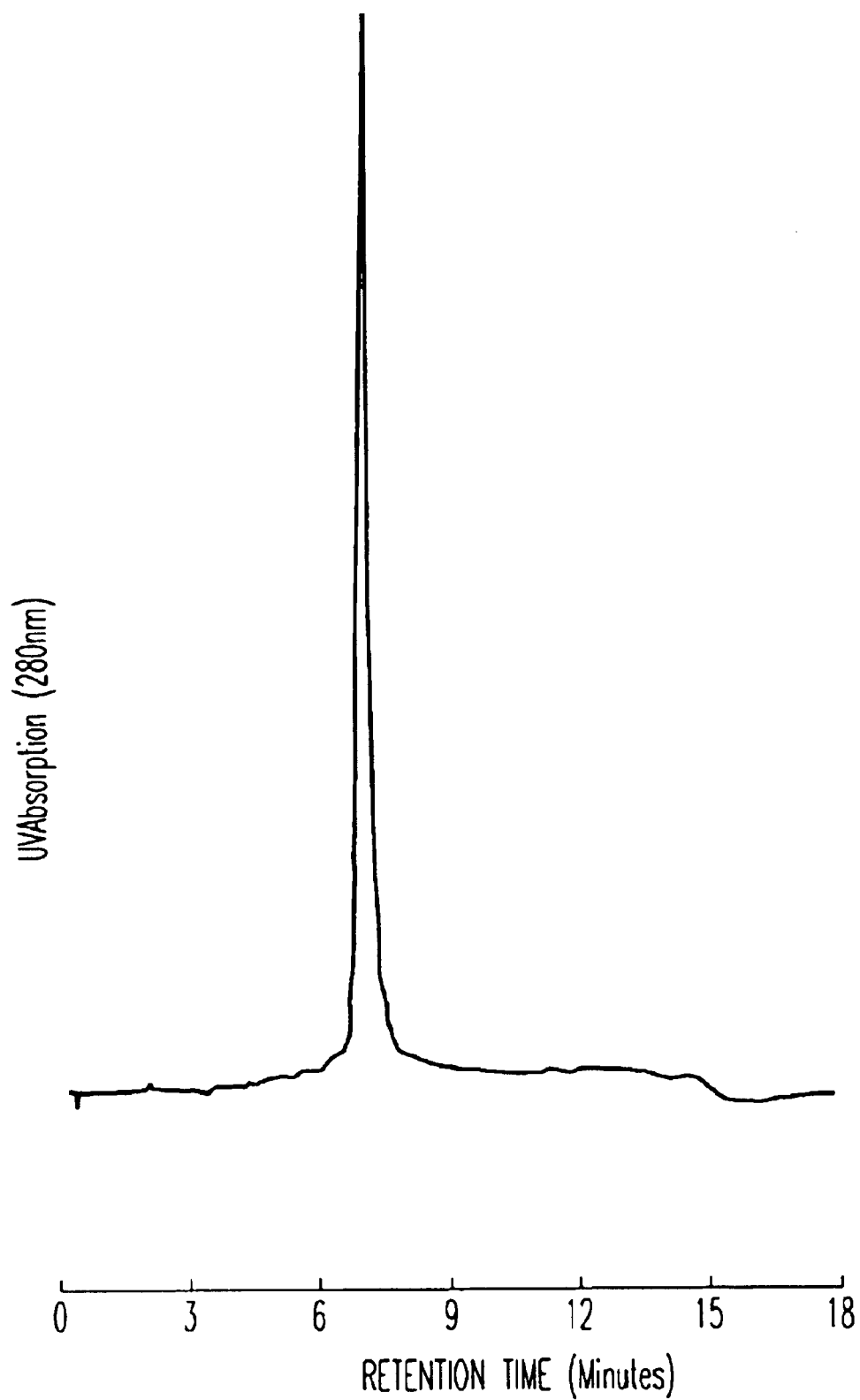

FIG. 7 shows the result of an anion exchange HPLC of purified human activin A fraction, performed in Example 2. The horizontal axis shows the retention time (minutes).

12 μg of purified human activin A were applied to an anion exchange HPLC (DEAE-NPR; TOSOH Corp.) and subjected to the elution with salt concentration gradient. The peak detected at ca. 7 min. of retention time corresponds to that of human activin A.

Figure 8:
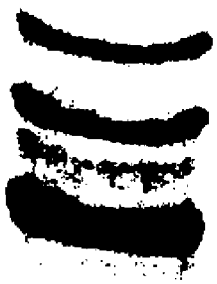
Figure 8:
Figure 8:
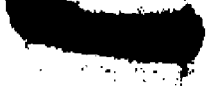
Figure 8:
Figure 8:
Figure 8:

FIG. 8 shows the result of SDS-PAGE of purified human activin A performed in Example 2.

21 μg and 21 ng of purified human activin A were each subjected to SDS-PAGE (PhastSystem; Amersham Pharmacia Biotech Limited) according to the standard method. The band detected at the mobility of molecular weight ca. 26,000 corresponds to that of human activin A.

Lane 1; Standard protein solution of 6 different molecular weights (94,000, 67,000, 43,000, 30,000, 20,000, and 14,400) (Molecular weight calibration kit LMW; Amersham Pharmacia Biotech Limited), Lane 2; Purified human activin A 21 μg, and Lane 3; Purified human activin A 21 ng.

FIG. 9 shows the comparative result on the purity of proteins obtained by Example 2 and the former (conventional) method (refer to Japanese Patent Kokai Publication JP-A-02-255098).

Each 12 mg of human activin A obtained in Example 2 and the former (conventional) method (refer to Japanese Patent Kokai Publication JP-A-02255098) were subjected to a cation exchange HPLC using SP-NPR column, and the protein purities were compared.

In the figure, (a) shows the result according to Example 2 and (b) shows that of the former method.

DETAILED DESCRIPTION OF THE PREFERRED EMBODIMENTS

Concerning the embodiments of the present invention, a detail of the production of purified human activin A is mainly explained as follows.

In the crude human activin which is a starting material used for the present invention, various crude human activin products such as crude human activin A, are included. Thus, the crude human activin may be a human activin containing at least one species of various impurities which is difficult to separate by the conventional purification method. There is no restriction to the species of impurities, and it is a superior point that a variant different in electrostatic character from the activin, a protein derived from a host, an antigenic substance and a pyrogen etc. derived from a host and/or a medium, a non-refolded aggregates in case of refolding, molecular variants based on the translational mistake and/or inappropriate post-translational processing of the gene, and degradation, modification and the like products produced in the purification process are all can be separated effectively, especially, this process is suitable for higher removal of a variant different in electrostatic character from the activin.

There are two categories in the above-mentioned variants contained in the raw materials for the human activin A to be purified. As described above in detail, roughly classifying, one is the variant which is already contained in the medium at the end of cultivation (it is due to the integration of incorrect amino acid in E coli. or abnormal modifications by the enzyme of E coli. after protein synthesis), and another is the variant produced in the purification process (it is due to the modification in the process of refolding or chromatography). Purification technologies used in the present invention exhibit the effectiveness particularly in the process of separating and removing the variant produced during the refolding process (in particular, deamidation products at high pH, for example the change of asparagine to aspartic acid in the molecule) from human activin A. Thus, concerning the purification method in the present invention, it is particularly effective in case of producing denatured human activin A in microorganisms, and refolding it artificially.

The following is an explanation in case of human activin A to be purified as an example.

A solution of crude human activin A refolded based on the method described in WO 97/23638 after subjecting to reduction, denaturation and extraction of tile inclusion body obtained from the recombinant microorganisms to which human activin A gene was introduced, can be used. In this method, at first, it is preferable to remove low molecular weight impurities from crude human activin A solution. As a method for removing low molecular weight impurities in this case, any method known for removing it, is applicable, briefly, general methods for substitution of buffer solution such as a ultra filtration method, a gel filtration chromatography method, and dialysis method and so on. At that time, by diluting crude human activin A solution previously, and concentrating it with the membrane of molecular weight cut off, 10,000 or so, it is possible to scale-up regardless of species of contents of impurities in the raw material.

The process for producing purified human activin in the present invention, is the method of purifying crude human activin with a cation exchange chromatography by concentration gradient elution method, in particular, by the chaotropic ion concentration gradient elution method, to produce human activin with improved purity.

Chaotropic ion is a kind of salt having the effect to break the higher order structure of protein. It is an ion such as NaSCN and $NaClO_4$, which has the property of improving water solubility of low molecular weight nonelectrolyte, protein etc., and of denaturing them by breaking the higher order structure of protein and nucleic acid (refer to Fundamental Experimental Method of Protein and Enzyme, p. 63, rev.2; Takeichi Horio, published by Nankodo, 1994). It is understood that such a character is caused by breaking the structure of water with ions produced by dissociation of the salt, and suppressing the decrease of entropy of water produced in the contact of a hydrophobic substance with water.

The fraction in which low molecular weight impurities are removed in this way, is adjusted to acidic pH value, preferably pH 2 to 4 or so (more preferably pH 2.5 to 3.5 or so), and then applied to the cation exchange column (for example, Resource-S; Amersham Pharmacia Biotech Limited) equilibrated under acidic condition, preferably pH 2 to 4 (more preferably pH 2.5 to 3.5), with a material containing water soluble organic solvent, preferably high concentration of water soluble organic solvent (for example, 20 to 60% organic solvent, preferably lower alcohol of carbon numbers 1 to 4 such as ethanol and isopropanol, acetonitrile, dimethyl sulfoxide, and dimethylformamide etc.), and not more than 0.2 M of the salt having chaotropic ion character (for example, Perchlorate such as $NaClO_4$ and $KClO_4$, and thiocyanate such as NaSCN and KSCN, etc.), and the human activin is eluted by salt concentration gradient. In tile salt concentration gradient, the salt concentration is raised to 0.2 to 0.4 M or so in the volume of not less than 10 column volumes, the variants etc. different in electrostatic character from the human activin are effectively removed, and thereby high concentration of human activin A can be produced at a high recovering yield.

Moreover, it is very advantageous for improving purification efficiency, to remove previously most of the impurities derived from raw materials and produced in the process until the refolding, by using preferably 2 steps of anion exchange chromatography as follows, before the application of an cation exchange chromatography, in order to reduce the burden of the purification with the cation exchange chromatography as described above.

After low molecular weight impurities have been removed (preferably, the buffer solution has been substituted at pH 9.5 to 10.5 or so by gel filtration chromatography method), 6 mg/mL-gel or so of the crude human activin is applied to an anion exchange column (for example, Q-SephaloseFF; Amersham Pharmacia Biotech Limited) having a natural polysaccharide as a base matrix, equilibrated with a buffer solution (for example, using 20 mM of 1,3-diaminopropane/HC1) of pH 9.5 to 10.5 or so containing a salt not more than 50 mM (for example, using NaCl), and after washing with the equilibrated buffer solution of about 5 column volumes, the buffer solution of pH 8.5 to 9.5 or so (for example, 20 mM of 1,3-diaminopropane/HCl) containing water soluble organic solvent (for example, using 5 to 25% of lower alcohol of carbon number 1 to 4 such as ethanol and isopropanol, acetonitrile, dimethyl sulfoxide, and dimethylformamide etc.) and a salt of not less than 0.1 M (for example, using NaCl), is substituted and thereby a human activin A fraction in which most of monomers and aggregates has been removed and which is concentrated to not less than 1 mg/mL, can be obtained. The buffer solution of this fraction is substituted with that of pH 9.5 to 10.5 or so (for example, 20 mM of 1,3-diaminopropane/HCl), and then 5 mg/mL-gel or so of this fraction is applied to an anion exchange column (for example,. Resource-Q; Amersham Pharmacia Biotech Limited) equilibrated with the buffer solution of pH 9.5 to 10.5 or so (for example, 20 mM of 1,3-diaminopropane/HCl) containing organic solvent (for example, 5–25% of organic solvent, preferably lower alcohol of carbon numbers 1 to 4 such as ethanol and isopropanol, acetonitrile, dimethyl sulfoxide, and dimethylformamide etc.) and a salt of not more than 50 mM (for example, using NaCl). By raising the salt concentration to not less than 0.1 M, and at the same time lowering pH value to around 8.5 to 9.5 in the elution volume of not less than 10 column volumes, variants which is difficult to be separated and removed in the cation exchange chromatography, can be removed.

As a final purification process, by purifying this fraction for example using the cation exchange chromatography according to Example 1, the human activin A having single electrostatic character can be produced in high concentration with high recovering yield. And the particle size of packing materials used for these chromatography is large, and it is possible to scale up by improving the column volume linearly.

Moreover, the purity of the fraction obtained finally, can be confirmed by reverse-phase HPLC (for example, using Nucleosil C8; GL Science Co.), anion exchange HPLC (for example, using DEAE-NPR; TOSOH Corp.), cation exchange HPLC (for example, using SP-NPR; TOSOH Corp.) and SDS-PAGE etc.

A highly purified human activin thus obtained, can be used easily as the drug product as described above, however, concerning the production of drug product, the technique for drug product which can be generally used and known in the field of drug manufacturing can be used.

EXAMPLES

Having generally described this invention, a further understanding can be obtained by reference to certain specific examples which are provided for purposes of illustration only and are not intended to be limiting unless otherwise specified.

Example 1

The denatured human activin A obtained from the recombinant *E. coli.* to which a human activin A gene was introduced, was refolded according to the method described in WO97/23638. After addition of equal volume of $H_2O$ to 250 mL of the refolding solution (12 mg of protein), the mixed solution was concentrated to one thirteenth of original volume by using the membrane of molecular weight cut off 10,000 ("OMEGA" manufactured by Filtron, U.S.A.). 11.5 mg of the protein were recovered by this membrane concentration procedure (96% yield), and the protein purity of the fraction measured by reverse-phase HPLC was 68%.

This fraction was applied to Sephadex G-25M (2.6ø×20 cm; Amersham Pharmacia Biotech Limited) equilibrated with 1.8 mM HCl, and 11.3 mg of the protein detected at A280 were recovered (98% yield). 5 mg of this fraction was applied to Resource-S (0.5ø×5 cm; Amersham Pharmacia Biotech Limited) equilibrated with the buffer solution of 40% acetonitrile, 0.18M $NaClO_4$, 20 mM sodium citrate, pH 3.0, washed with 6 mL of the equilibrated buffer solution, and then subjected to the concentration gradient of $NaClO_4$ adjusted at 0.24 M after eleven minutes in the flow rate of 1.5 mL/min. 3.7 mg of protein detected at A280 were recovered (74% yield, refer to the chromatography in FIG. 1*b*).

When a cation exchange chromatography using NaCl instead of $NaClO_4$ as a salt for elution (other conditions except for species and concentration of salt are same as above) was performed, the ability to separate impurities at front of the peak, was lowered (refer to the chromatography in FIG. 1*a*) compared to the condition using $NaClO_4$, and the recovery was also lowered (51% yield) that much.

Example 2

By using the same condition as described in Example 1, 37.0 mg of the membrane concentrated fraction were obtained from the refolding solution. This fraction was applied to Sephadex G-25M (1.6ø×10 cm; Amersham Pharmacia Biotech Limited) equilibrated with 20 mM 1,3-diaminopropane/HCl containing 30 mM NaCl, and 36.3 mg of protein detected at A280 were recovered (98% yield). 36.0 mg of this fraction was applied to Q-Sephalose FF (1.6ø×3 cm; Amersham Pharmacia Biotech Limited) equilibrated with 20 mM 1,3-diaminopropane/HCl (pH 10) containing 30 mM NaCl, and thereby the substitution was performed. It was washed with approximately 30 mL of the equilibrated buffer solution, and then was made substitution with the buffer solution of 0.3 M NaCl, 12% acetonitrile, 20 mM 1,3-diaminopropane/HCl (pH 9.0) to recover 34.9 mg of protein detected at A280 (97% yield, refer to FIG. 2).

About the recovered fraction, the protein purity measured by reverse-phase HPLC (Nucleosil C8; GL Science Co.), anion exchange HPLC (DEAENPR; TOSOH Corp.) and cation exchange HPLC (SP-NPR; TOSOH Corp.) was 97%, 65% and 75% respectively. 34 mg of this fraction was applied to Sephadex G-25M (1.6ø×17 cm; Amersham Pharmacia Biotech Limited) equilibrated with 20 mM 1,3-diaminopropane/HCl (pH 10), and 33.3 mg of protein detected at A280 were recovered (98%,, yield). 5 mg of this fraction was applied to Resource-Q (0.5ø×5 cm; Amersham Pharmacia Biotech Limited) equilibrated with the buffer solution of 10% acetonitrile, 30 mM NaCl, 20 mM 1,3-diaminopropane/HCl (pH 9.8).

After washing with approximately 6 mL of the equilibrated buffer solution, it was subjected to the concentration gradient of NaCl and pH gradient adjusted at 10% acetonitrile, 0.3 M NaCl, 20 mM 1,3-diaminopropane/HCl (pH 9.0) after eleven minutes in the flow rate of 1.5 mL/min. This procedure was repeated twice, and the sum of 5.5 mg protein detected at A280 were recovered (55% yield, refer to FIG. 3).

About this fraction, the protein purity measured by anion exchange HPLC (DEAE-NPR; TOSOH Corp.) and cation exchange HPLC (SP-NPR; TOSOH Corp.) was 99% and 88% respectively. This fraction was further applied to Sephadex G-25M (1.6ø×5 cm; Amersham Pharmacia Biotech Limited) equilibrated with 1.8 mM HCl, and then 5.4 mg of protein detected at A280 were recovered (98% yield). 5 mg of this fraction were applied to Resource-S (0.5ø×5 cm; Amersham Pharmacia Biotech Limited) according to Example 1, and 3.9 mg of protein detected at A280 were recovered (78% yield, refer to FIG. 4).

This fraction was applied to Sephadex G-25M (1.6ø×5 cm; Amersham Pharmacia Biotech Limited) equilibrated with 1.8 mL HCl and 3.9 mg of the protein detected at A280 was recovered (99% yield). The results performed for the analysis of reverse-phase HPLC (Nucleosil C8; GL Science Co.), anion exchange HPLC (DEAE-NPR; TOSOH Corp.), cation exchange HPLC (SP-NPR; TOSOH Corp.) and SDS-PAGE on this fraction was shown in FIGS. 5 to 8. In the reverse-phase HPLC (refer to FIG. 5), cation exchange HPLC (refer to FIG. 6), and anion exchange HPLC (refer to FIG. 7), any peak except for that of human activin A was not detected, and it was confirmed that no impurities were detected by these analytical methods. In addition, by SDS-PAGE (refer to FIG. 8), no band except for that of human activin A was detected in the lane loaded 2.1 μg of human activin A (lane 2). It was confirmed that impurities contained in lane 2 were 0.1% or less as only one component, in view of the fact that a band of human activin A was detected on the lane 3 loaded with 21 ng of human activin A.

Table 1 showed the outline of the result of the present examples containing the membrane concentration procedure described in Example 1, and Table 2 showed the analytical conditions of each HPLC of FIGS. 5 to 8, and SDS-PAGE.

Figure 9A:
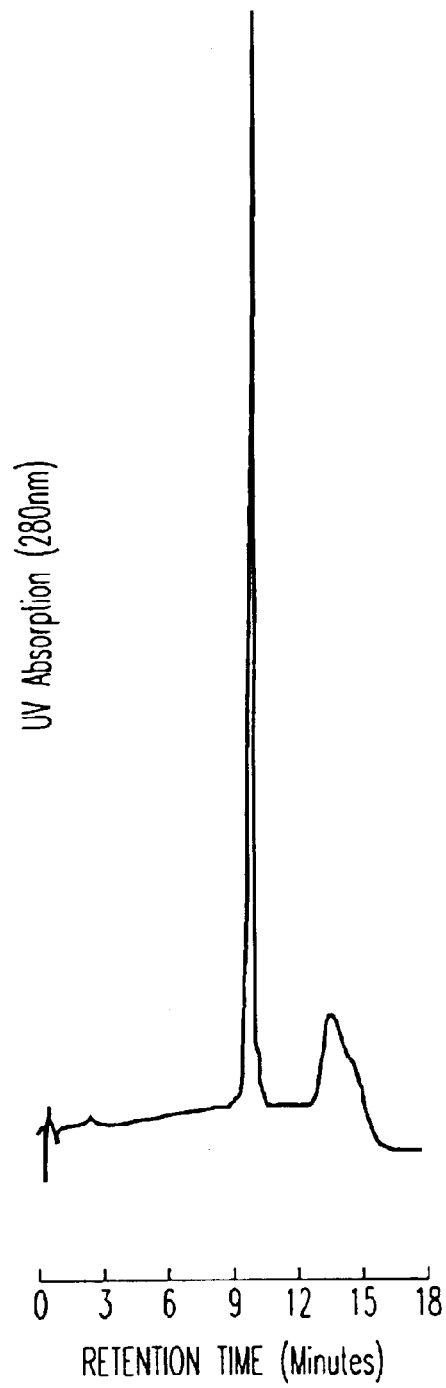
Figure 9B:
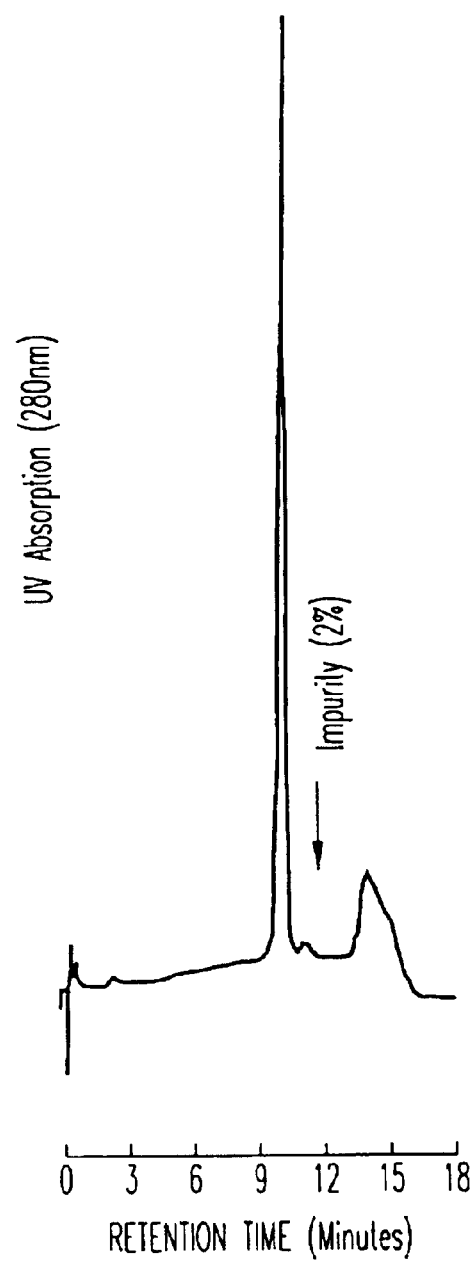

Protein purity of purified human activin A obtained by former purification method (refer to Japanese Patent Kokai Publication JP-A-02-255098) and that of purified human activin A obtained in the present Example 2 were compared by using cation exchange HPLC (refer to FIG. 9). In the former (conventional) purification method (FIG. 9*b*), about 2% of impurities except for purified human activin A remained. However, no impurities was detected in the purified human activin A of the present Example 2 (FIG. 9*a*), and thereby the purity thereof was supposed to be at least 99%, and usefulness of the present purification method was elucidated.

TABLE 1

Outline of the purification results of human activin A

| Process and others | Used protein (mg) | Recovered protein (mg) | Total yield of recovered protein (%) |
|---|---|---|---|
| Solution of crude human activin A | 39.0 | 39.0 | 100 |
| Membrane concentration | 39.0(*) | 37.4(*) | 96(*) |
| Gel filtration chromatography (Sephadex G-25M) | 37.0 | 36.3 | 94 |
| Anion exchange chromatography (Q-Sephalose FF) | 36.0 | 34.9 | 91 |
| Gel filtration chromatography (Sephadex G-25M) | 34.9 | 33.3 | 89 |
| Anion exchange chromatography (Resource-Q) (2 times execution) | 10.0 | 5.5 | 49 |
| Gel filtration chromatography (Sephadex G-25M) | 5.5 | 5.4 | 48 |

(*): Results of purification by membrane concentration according to Example 1.

TABLE 2

Conditions of each HPLC and SDS-PAGE analysis (1) Reverse-phase HPLC
  Column: Nucleosil 300-5C8 (4.6 mm ø × 100 mm; GL Science Co.)
  Solvent A: 0.13% Heptafluorobutyric acid
  Solvent B: 0.13% Heptafluorobutyric acid, 80% Acetonitrile
  Elution program:

| Time | Solvent A | Solvent B |
|---|---|---|
| 0 min. | 65% | 35% |
| 16 | 25 | 75 |
| 17 | 10 | 90 |
| 18 | 0 | 100 |
| 22 | 0 | 100 |

Flow rate: 1 mL/min.
  Charged amount: human activin A 7 μg
  Detection: UV absorption (280 nm)
  HPLC system: Low pressure gradient HPLC system (HITACHI, Japan)
(2) Cation exchange HPLC
  Column: SP-NPR (4.6 mm ø × 30 mm; TOSOH Corp.)
  Solvent A: 40% Acetonitrile, 20 mM Sodium citrate (pH 3.0)
  Solvent B: 40% Acetonitrile, 0.1M $NaClO_4$, 20 mM Sodium citrate (pH 3.0)
  Elution program:

| Time | Solvent A | Solvent B |
|---|---|---|
| 0 min. | 70% | 30% |
| 1 | 70 | 30 |
| 11 | 50 | 50 |
| 11.1 | 0 | 100 |
| 13 | 0 | 100 |

Charged amount: human activin A 7 μg
  Flow rate, Detection, and HPLC system are same as above (1)
(3) Anion exchange HPLC
  Column: DEAE-NPR (4.6 mm ø × 30 mm; TOSOH Corp.)
  Solvent A: 10% Acetonitrile, 20 mM 1,3-diaminopropane/HCl (pH 10)
  Solvent B: 10% Acetonitrile, 0.5M NaCl, 20 mM 1,3-diaminopropane/HCl (pH 9)
  Elution program:

| Time | Solvent A | Solvent B |
|---|---|---|
| 0 min. | 100% | 0% |
| 1 | 100 | 0 |
| 11 | 0 | 100 |
| 13 | 0 | 100 |

Flow rate, Detection, Charged amount and HPLC system are same as above (2)
(4) SDS-PAGE
  Automatic electrophoresis system, PhastSystem (Amersham Pharmacia Biotech Limited). Method of SDS-PAGE as described in user's manual (Diamine-Silver staining method as staining).

As clearly shown in FIG. 8, Table 1 and Table 2, it is understood that highly purified human activin can be produced and obtained by using the purification method in the production method of the present invention. Concerning the purity, the result of electrophoresis in FIG. 8 indicates that impurities in the order of one thousands are not included. Thus the purity is at least 99.9%, that is, having a high purity not less than 99.9%.

As used herein, the term "purified" human activin means a human activin having a purity of at least 99.0%.

According to a process for the production in the present invention, which comprises subjecting a crude human activin to a purification procedure involving a cation exchange chromatography by a concentration gradient elution method, a highly pure human activin, which could not be obtained by the former process, can be produced. Thus the pharmaceutical use of human activin can be expected.

Having now fully described this invention, it will be apparent to one of ordinary skill in the art that many changes and modifications can be made thereto without departing from the spirit or scope of the invention as set forth herein.

This application is a continuation of International Application No. PCT/JP99/02680 filed on May 20, 1999, and claims priority to Japanese Patent Application No. 10-159943 filed on May 25, 1998. each of which are incorporated herein by reference in their entirety.

What is claimed as new and desired to be secured by Letters Patent of the United States is:

1. A process for purifying human activin, comprising
  applying crude human activin to a cation exchange column equilibrated with a water soluble organic solvent; and
  eluting the human activin with an increasing chaotropic ion concentration gradient.

2. The process according to claim 1 wherein the human activin purified is a human activin A.

3. The process according to claim 1 wherein the purity of the human activin obtained by the process is at least 99.0%.

4. The process according to claim 1 wherein the purity of the human activin obtained by the process is at least 99.9%.

5. The process according to claim 1, wherein the cation exchange column is further equilibrated with a perchlorate salt.

6. The process according to claim 5 wherein the perchlorate salt is at least one of sodium perchlorate or potassium perchlorate.

7. The process according to claim 1, wherein the cation exchange column is further equilibrated with a thiocyanate salt.

8. The process according to claim 7, wherein the thiocyanate salt is at least one of sodium thiocyanate or potassium thiocyanate.

9. The process according to claim 1, wherein the chaotropic concentration gradient comprises a perchlorate salt.

10. The process according to claim 9, wherein the perchlorate salt is at least one of sodium perchlorate or potassium perchlorate.

11. The process according to claim 1, wherein the chaotropic concentration gradient comprises a thiocyanate salt.

12. The process according to claim 11, wherein the thiocyanate salt is at least one of sodium thiocyanate or potassium thiocyanate.

13. The process according to claim 1 wherein said cation exchange column is equilibrated to an acidic pH.

14. The process according to claim 13, wherein said organic solvent contains at least one member selected from the group consisting of a lower alcohol, acetonitrile, dimethyl sulfoxide and dimethylformamide.

15. The process according to claim 14, wherein the concentration of the lower alcohol, acetonitrile, dimethyl sulfoxide or dimethylformamide is at least 20 volume %.

16. The process according to claim 15, wherein the concentration is from 20 to 60 volume %.

* * * * *